United States Patent
Teo et al.

(10) Patent No.: US 6,540,763 B2
(45) Date of Patent: Apr. 1, 2003

(54) LANCET DEVICE WITH RETRACTABLE SHARPS MEMBER

(75) Inventors: John Hock Meng Teo; Liak Hiong Goh, both of Singapore (SG)

(73) Assignee: Medisys Asia Pacific PTE Ltd., Singapore (SG)

( * ) Notice: Subject to any disclaimer, the term of this patent is extended or adjusted under 35 U.S.C. 154(b) by 51 days.

(21) Appl. No.: 09/788,932

(22) Filed: Feb. 20, 2001

(65) Prior Publication Data

US 2002/0128608 A1 Sep. 12, 2002

(51) Int. Cl.[7] .............................................. A61B 17/34
(52) U.S. Cl. ........................................................ 606/182
(58) Field of Search ................................ 606/167, 171, 606/172, 181, 182, 185; 604/110, 192, 194, 195, 196, 197, 198, 187, 263

(56) References Cited

U.S. PATENT DOCUMENTS

| | | | | |
|---|---|---|---|---|
| 4,677,979 A | * | 7/1987 | Burns .......................... | 606/172 |
| 4,775,369 A | | 10/1988 | Schartz ........................ | 604/263 |
| 4,883,068 A | | 11/1989 | Dechow ....................... | 128/760 |
| 5,045,066 A | | 9/1991 | Scheuble et al. ............ | 604/198 |
| 5,086,780 A | | 2/1992 | Schmitt ........................ | 128/763 |
| 5,137,521 A | | 8/1992 | Wilkins ........................ | 604/198 |
| 5,336,187 A | | 8/1994 | Terry et al. .................. | 604/110 |
| 5,439,473 A | * | 8/1995 | Jorgensen .................... | 604/136 |
| 5,630,803 A | | 5/1997 | Tamaro ........................ | 604/263 |
| 5,666,966 A | | 9/1997 | Horie et al. ................. | 128/760 |
| 5,746,761 A | * | 5/1998 | Turchin ........................ | 606/181 |
| 5,873,856 A | | 2/1999 | Hjertman et al. ............ | 604/117 |
| 6,053,930 A | | 4/2000 | Ruppert ....................... | 606/181 |
| 6,136,013 A | * | 10/2000 | Marshall et al. ............. | 606/167 |
| 6,248,120 B1 | * | 6/2001 | Wyszogrodzki .............. | 606/182 |
| 6,258,112 B1 | * | 7/2001 | Schraga ....................... | 606/181 |

FOREIGN PATENT DOCUMENTS

WO WO 93 09723 5/1993

* cited by examiner

Primary Examiner—Lesley D. Morris
Assistant Examiner—Patrick Buechner
(74) Attorney, Agent, or Firm—Fulbright & Jaworski L.L.P.

(57) ABSTRACT

A retractable sharps assembly comprising a housing and a sharps unit. The housing comprises first and second open ends and a shoulder proximate the first end. The sharps unit generally comprises a frame, a shelf having a sharps member extending therefrom positioned in the frame, and at least one elastic member extending between the shelf and the forward end. As the frame is inserted into and moved forward in the hollow housing, the shelf is retained by the shoulder such that the elastic member is loaded between the shelf and forward end. A trigger mechanism interacts with the shoulder and disengages the shelf. The load in the elastic member drives the sharps member towards the forward end and through the second end opening, and simultaneously compresses the elastic member. The elastic member thereafter relaxes to retract the sharps member within the housing.

17 Claims, 3 Drawing Sheets

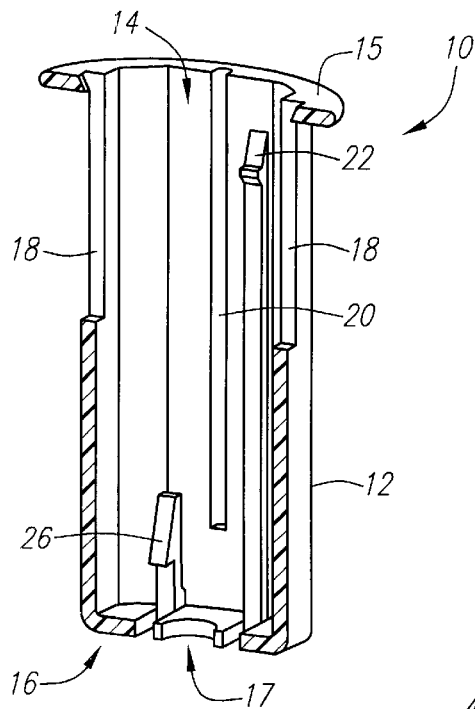
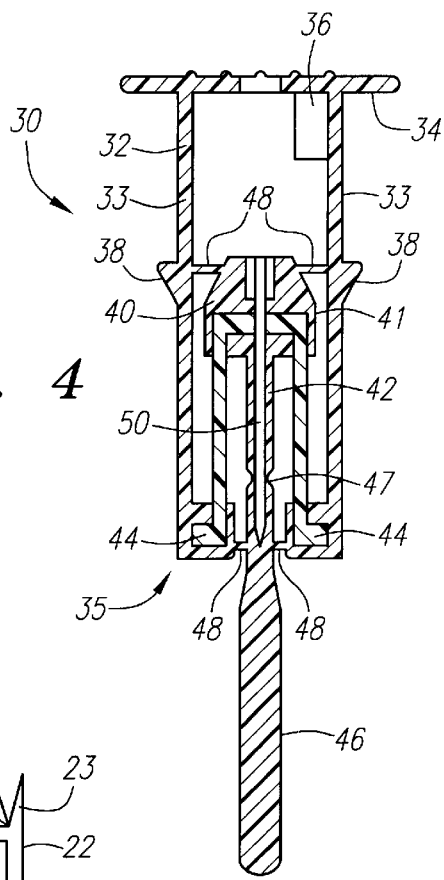
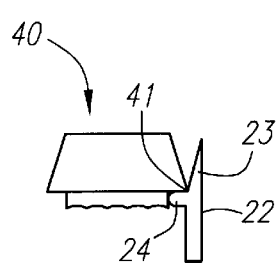
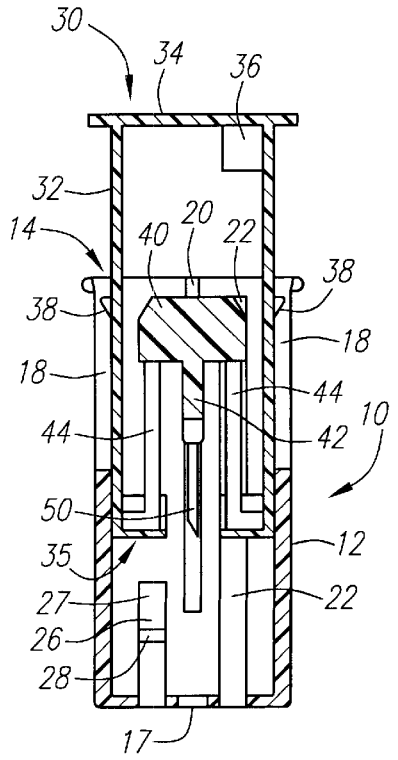
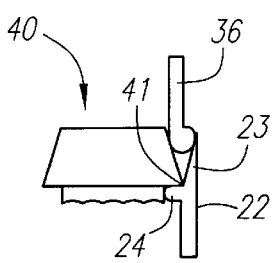
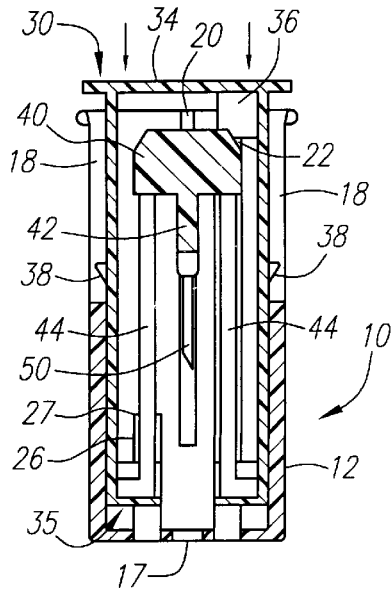
FIG. 3
FIG. 4
FIG. 6
FIG. 5
FIG. 8
FIG. 7

LANCET DEVICE WITH RETRACTABLE SHARPS MEMBER

BACKGROUND

The present invention relates generally to protection against an accidental sharps injury or stick. More particularly, the present invention relates to a retractable lancet device for protection from an accidental sharps injury or stick from a used sharps member of the type commonly associated with finger sticks.

For some time, the art has recognized the desirability of protecting personnel from accidental sharps injuries or needle sticks. More recently, concerns have been expressed about the possibility of transmitting serious or potentially fatal infection as a result of such accidents. Most recently, legislation requiring the use of safe needle technology is pending in a number of states and before the Occupation Safety and Health Administration. Although the art has recognized the desirability of protecting against accidental sharps injuries or needle sticks, it is believed that practical protective devices, particularly lancet devices, are still not available.

Various methods of providing a preloaded retraction assembly which permit one hand operation are known. See for example U.S. Pat. Nos. 5,209,739, 5,928,200 and 5,836,917, European Patent No. 0 480 862 A1, and commonly assigned PCT Application Nos. PCT/US97/20646 and PCT/US99/29541.

Another concern with prior art devices is the complicated and costly manufacturing processes. With the tremendous number of syringes and other needle devices used by the medical community, any substantial rise in cost of the products is undesirable and generally unacceptable.

Accordingly, there is a need for a lancet device having an automatically retracted used sharps member that can be used in a conventional manner and does not require elaborate manufacturing.

SUMMARY

The present invention relates to a retractable sharps assembly comprising a generally hollow housing and a sharps unit. The housing comprises first and second ends, each end with an opening into the housing, and a shoulder proximate the first end and extending into the hollow housing. The sharps unit comprises a frame having forward and rear ends and configured such that the forward end is received through the first end and into the hollow housing. A trigger mechanism extends from the frame adjacent the rear end. A shelf having a sharps member extending therefrom is positioned in the frame and has a rest position a given distance from the forward end. At least one elastic member extends between the shelf and the forward end. As the frame is inserted into and moved forward in the hollow housing, the shelf is initially retained by the shoulder such that the elastic member is loaded between the shelf and forward end until such time as the trigger mechanism interacts with the shoulder causing the shelf to disengage therefrom. The stored energy in the elastic member drives the sharps member towards the forward end and through the second end opening as the shelf moves further inwardly from the rest position toward the forward end, thereby compressing the elastic member. The elastic thereafter relaxes to retract the sharps member within the housing.

BRIEF DESCRIPTION OF THE DRAWINGS

FIG. 3 is a section view taken along line 3—3 in FIG. 1.

FIG. 4 is a section view taken along line 4—4 in FIG. 1.

FIG. 5 is a section view taken along line 5—5 in FIG. 2.

FIG. 6 is an elevation view illustrating the interaction of the shelf and shoulder of the preferred embodiment when the frame is in the position of FIG. 5.

FIG. 7 is a section view similar to FIG. 5 with the frame partially depressed.

FIG. 8 is an elevation view illustrating the interaction of the shelf and shoulder of the preferred embodiment when the frame is in the position of FIG. 7.

DETAILED DESCRIPTION OF TABLE PREFERRED EMBODIMENT

The preferred embodiment will be described with reference to drawing figures where the numerals represent like elements throughout.

Figures 1, 2:
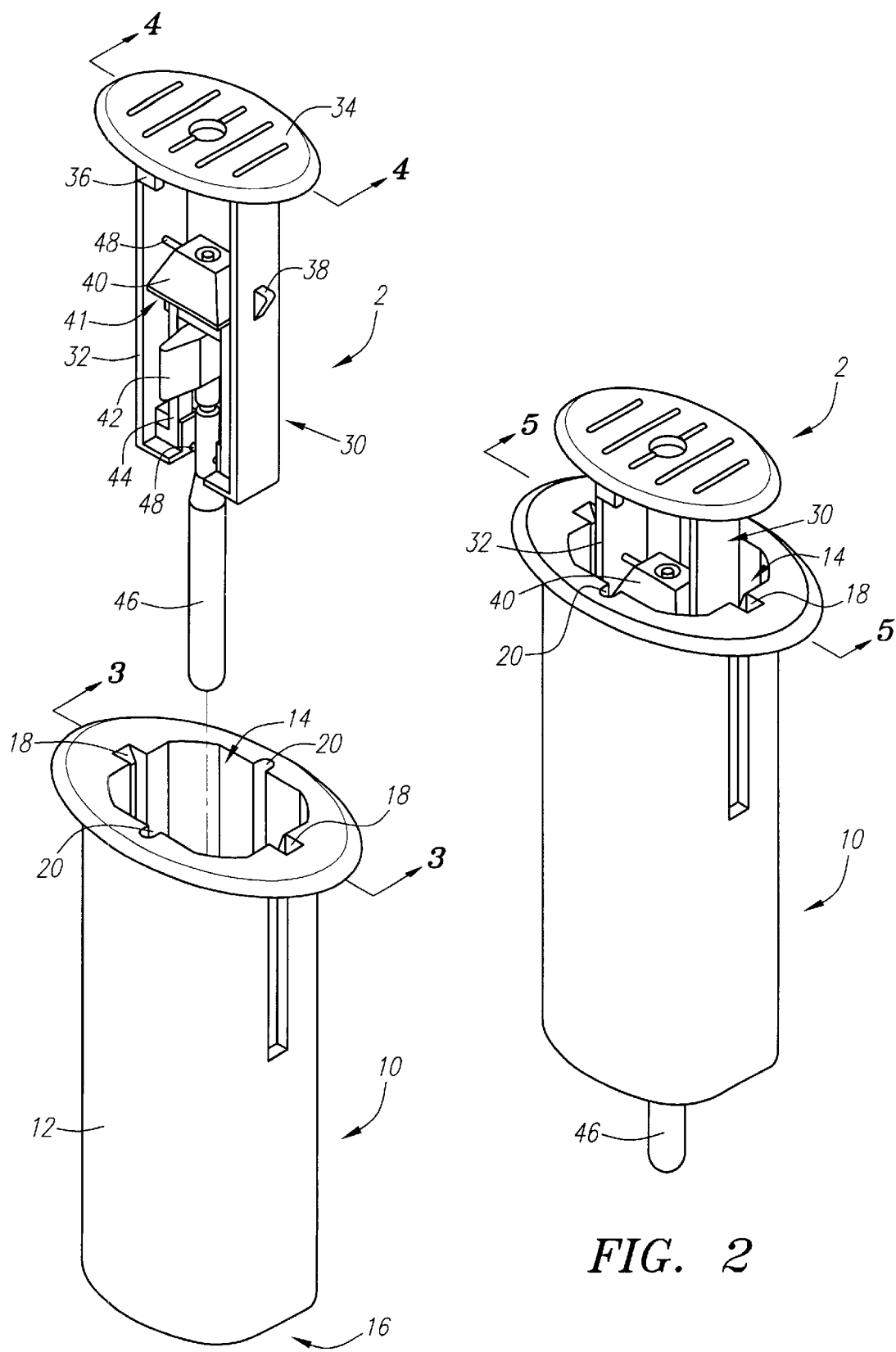
FIG. 1 is an isometric view of the housing and sharps unit of the preferred embodiment of the retractable sharps assembly prior to assembly.
FIG. 2 is an isometric view of the housing and sharps unit of the preferred embodiment assembled.

Referring to FIGS. 1 and 2, the preferred retractable sharps assembly 2 comprises a housing 10 and a sharps unit 30. The housing 10 has a substantially open end 14 configured to receive the sharps unit 30 as illustrated in FIG. 2. The housing 10 and the sharps unit 30 will be described in more detail with reference to FIGS. 3 and 4, respectively.

Referring to FIG. 3, the preferred housing 10 comprises a hollow body 12 having the substantially open end 14 and an opposite, generally closed end 16 with an opening 17 therethrough. Opposed guide slots 18 are defined along the body 12 to receive guide projections of the sharps unit as will be described hereinafter. A second pair of guide slots 20 are also provided for receiving guides provided along the sharps support shelf, as will be described hereinafter. While the preferred embodiments have the guide slots 18, 20 along the housing 10, the housing 10 may instead be provided with the projections and the corresponding sharps unit 30 components provided with slots or the like. Additionally, it is possible to omit the sharps unit guide slots 18 by configuring the housing opening 14 and the sharps unit frame 32 to correspond, for example, by providing both elements with complementary rectangular configurations. The preferred hollow body 12 has a oval configuration, but other shapes, for example, square, rectangular, or circular, can also be used. The housing 10 further includes a retaining shoulder 22 and a latch 26, the functions of which will be described hereinafter.

Referring to FIG. 4, the preferred sharps unit 30 generally comprises a frame 32, a trigger mechanism 36, a pair of elastic members 44, a sharps carrier defining a sharps support shelf 40 and a sharps member 50. The preferred frame 32 has a pair of opposed side rails 33 extending between a thumb pad 34 and a frame forward end 35. A guide projection 38 extends from each rail 33 and is configured to be received within a corresponding housing guide slot 18. Such interaction helps stabilize the sharps unit 30 relative to the housing 10. While this is the preferred frame configuration, other configurations are can also be used. The trigger mechanism 36 depends from the thumb pad 34 and will be described in more detail hereinafter.

The sharps member 50 is maintained by the sharps support shelf 40 which is positioned within the frame 32 with the sharps member 50 projecting toward the frame forward end 35. The pair of elastic members 44 extend between the frame forward end 35 and the support shelf 40. The elastic members 44 are manufactured from an elastic material which can be loaded by both stretching and compression. An example of a suitable material is Kraton™ G2706 manufactured by Shell Oil. While the preferred embodiment includes two elastic members 44, any number of elastic members, including one, may be used.

The sharps unit 30 is preferably manufactured using a multi-shot injection molding process similar to that described in PCT International Application No. PCT/US99/29541, commonly assigned with the present invention. During such process, the support shelf's 40 position is maintained by frangible rods 48 extending between it and the rails 33. The rods 48 are preferably sufficiently fragile such that the assembly 2 is packaged with the rods 48 intact, but simply break upon depression of the frame 32 during use. However, if desired, the rods 48 may be removed in a post-molding process prior to assembly. In such a case, the support shelf 40 will still be maintained in position as the elastic members 44 are sufficiently rigid to support the shelf 40 away from the frame forward end 35. To further stabilize the support shelf 40, a tapered guide block 42 extends therefrom, as shown in FIG. 1. The block 42 is configured to be received in and move along the shelf guide slots 20 in the housing 10. The support shelf 40 also has a support edge 41 which will be described hereinafter.

The preferred sharps unit 30 also includes a removable cap 46 positioned about the forward end of the sharps member 50 and attached to a portion depending from the guide block 42 at a frangible junction 47. The cap 46 may also be supported by a pair of frangible rods 48. To remove the cap 46, the cap 46 is twisted or the like to sever the frangible junction 47 and rods 48.

Having described the components of the preferred embodiment, operation of the assembly 2 will be described with reference to FIGS. 5–13.

With reference to FIGS. 5 and 6, the sharps unit 30 is positioned in the housing 10 by passing the frame forward end 35 through the opening 14. As the sharps unit 30 moves into the housing 10, the support edge 41 of the support shelf 40 catches and is retained by a projection portion 24 of the shoulder 22. See FIG. 6. This is the preferred shipping and storage position of the assembly 2. The elastic members 44 are in a relaxed state, while maintaining the sharps member 50 in a position ready for use. As explained above, the assembly 2 preferably includes a cap 46, but such is not necessary. If such is present, it can simply be removed prior to use as explained above.

When ready for use, a user aligns the housing with the desired target, for example, a finger, and begins depressing the frame 32 by applying pressure to the thumb pad 34 as indicated by the arrows in FIG. 7. As explained above, the frangible rods 48 may or may not remain. If the rods 48 are present, they will simply yield to the depression pressure and fracture, thereby allowing the frame 32 to move forward into the housing 10. Referring to FIGS. 7 and 8, as the frame 32 is initially depressed, the support edge 41 remains engaged with the shoulder projection 24. As a result, the elastic members 44 are tensioned between the forward moving forward end 35 and the retained shelf 40.

Figure 9:
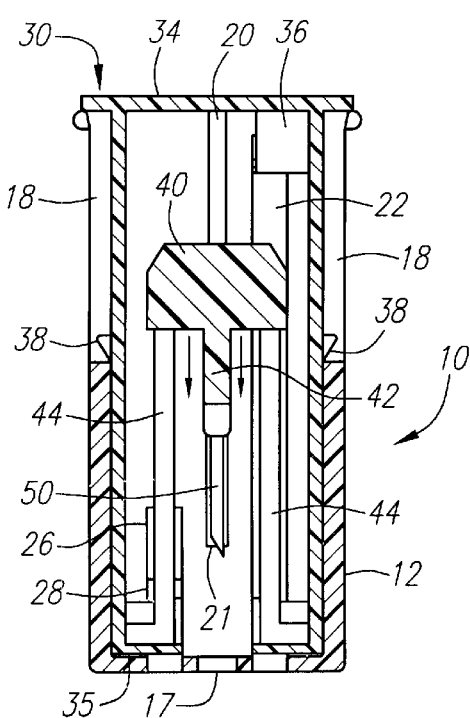
FIG. 9 is a section view similar to FIG. 5 with the frame completely depressed.
Figure 10:
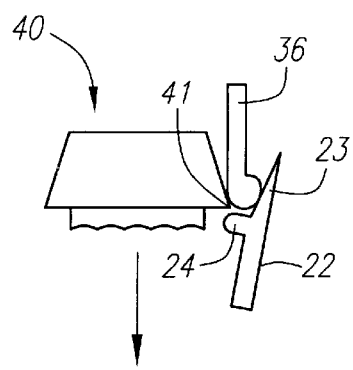
FIGS. 10 and 11 are elevation views illustrating the progressive interaction of the shelf and shoulder of the preferred embodiment as the frame is moved to the position of FIG. 9.
Figure 11:
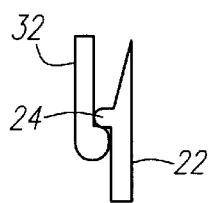

Referring to FIGS. 9–11, as the frame 32 is further depressed, the trigger mechanism 36 engages the sloped portion 23 of the shoulder 22, proceeds to disengage the projection 24 from the support edge 41, and then engages the underside of the projection 24 to lock the frame 32 within the housing 10. Upon disengagement of the support edge 41, the tensioned elastic members 44 cause the support shelf 40, and thereby the sharps member 50, to fire forward, as indicated by the arrows in FIG. 9.

Figure 12:
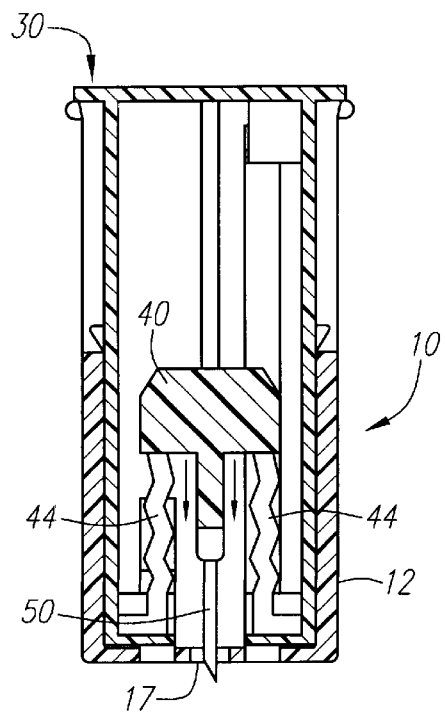
FIGS. 12 and 13 are section views similar to FIG. 5 showing the movement of the shelf and sharps member of the preferred embodiment upon triggering.
Figure 13:
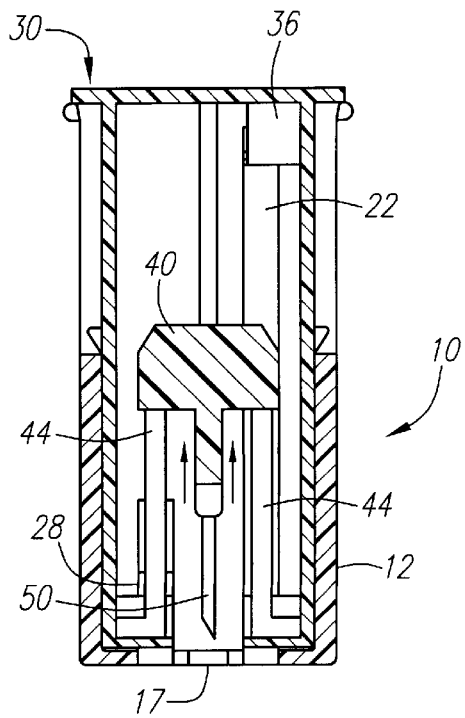

Referring to FIG. 12, the sharps member 50 extends from the housing opening 17, thereby engaging the desired target. The shelf guide slots 20 preferably have a bottom shelf 21, see FIG. 9, which defines the limit of forward movement of the support shelf 40 and thereby the sharps member 50. As the support shelf 40 moves to the forward limit, the elastic members 44 become compressed. The compressed elastic members 44 thereafter relax, as illustrated in FIG. 13, and thereby retract the shelf 40 and sharps member 50 back into the housing 10.

What is claimed is:

1. A retractable sharps assembly comprising:
   a generally hollow housing comprising first and second ends, each end with an opening into the housing;
   a shoulder proximate the first end extending into the hollow housing;
   a sharps unit comprising a frame having forward and rear ends and configured such that the forward end is received through the first end and into the hollow housing;
   a trigger mechanism adjacent to the frame rear end;
   a shelf positioned in the frame and having a rest position a given distance from the forward end;
   an elastic member extending between the shelf and the forward end; and
   a sharps member extending from the shelf toward the forward end;
   whereby as the frame forward end is inserted into and moved forward in the hollow housing, the shelf is initially retained by the shoulder such that the elastic member is loaded between the shelf and forward end until such time as the trigger mechanism interacts with the shoulder causing the shelf to disengage therefrom and thereby causing stored energy in the elastic member to drive the sharps member towards the forward end and through the second end opening as the shelf moves within the given distance, thereby compressing the elastic member, the elastic thereafter relaxing to retract the sharps member within the housing.

2. A retractable sharps assembly comprising
   a housing including a first end having a first opening therethrough and a shoulder in the housing facing away from the first end;
   a sharps unit including a frame slideably mounted in the housing to move toward and away from the first end, a trigger mechanism fixed to move with the frame, a sharps carrier slideably mounted in the frame toward and away from the first end and engageable with the shoulder, a sharps member fixed to move with the sharps carrier and extending toward the first opening, and an elastic member attached at one end to the frame and at the other end to the sharps carrier, the sharps member being within the housing with the frame extending fully toward the first end and the elastic member relaxed, the elastic member being stressed with the frame extending substantially fully toward the first end and the sharps carrier engaged with the shoulder, the trigger mechanism engaging the sharps carrier with the frame extending substantially fully toward the first end to release the sharps carrier from the shoulder, the sharps member being extendable from the housing through the first opening with the elastic member stressed.

3. The retractable sharps assembly of claim 2, the housing further including a second opening, the frame extending through the second opening and having a thumb pad fixed to the frame positioned outwardly of the housing.

4. The retractable sharps assembly of claim 3, the first and second openings being at opposite ends of the housing.

5. The retractable sharps assembly of claim 2, the elastic member being attached to the frame near the first end with the frame extending fully toward the first end and the elastic member being attached to the sharps carrier within the housing displaced from the first end.

6. The retractable sharps assembly of claim 2 further comprising a latch fixed to the housing and engaging the frame with the frame fully extended to the first end of the housing.

7. The retractable sharps assembly of claim 2 further comprising a cap removably positioned over the sharps member and extending through the first opening and outwardly of the housing.

8. The retractable sharps assembly of claim 7, the cap being frangibly coupled with the frame.

9. The retractable sharps assembly of claim 2, the housing further including first parallel guide slots, the frame including guide projections extending from the frame to engage the first parallel guide slots, respectively, with the sharps unit in the housing.

10. The retractable sharps assembly of claim 9, the housing further including second parallel guide slots, the sharps carrier having a block extending to engage the second parallel guide slots.

11. The retractable sharps assembly of claim 2, the sharps unit further including frangible rods extending between the sharps carrier and the frame.

12. The retractable sharps assembly of claim 11 further comprising
    a cap removably positioned over the sharps member and extending through the first opening to outwardly of the housing, the cap being frangibly coupled with the frame.

13. A retractable sharps assembly comprising
    a housing including a first end having a first opening therethrough, a second opening at a second end of the housing opposite the first opening and a shoulder in the housing facing away from the first end;
    a sharps unit including a frame slideably mounted in the housing to move toward and away from the first end and extending through the second opening and having a thumb pad positioned outwardly of the housing, a trigger mechanism fixed to move with the frame, a sharps carrier slideably mounted in the frame toward and away from the first end and engageable with shoulder, a sharps member fixed to move with the sharps carrier and extending toward the first opening, and an elastic member attached at one end to the frame near the first end with the frame extending fully toward the first end and at the other end to the sharps carrier within the housing displaced from the list end, the sharps member being within the housing with the frame extending fully toward the first end and the elastic member relaxed, the elastic member being stressed with the frame extending substantially fully toward the first end and the sharps carrier engaged with the shoulder, the trigger mechanism engaging the sharps carrier with the frame extending substantially fully toward the first end to release the sharps carrier from the shoulder, the sharps member being extendable from the housing through the first opening with the elastic member stressed.

14. The retractable sharps assembly of claim 13 further comprising a latch fixed to the housing and engaging the frame with the frame fully extended to the first end of the housing.

15. The retractable sharps assembly of claim 13 further comprising
    a cap removably positioned over the sharps member and extending through the first opening to outwardly of the housing.

16. The retractable sharps assembly of claim 13, the housing further including first parallel guide slots, the frame including guide projections extending from the frame to engage the first parallel guide slots, respectively, with the sharps unit in the housing, and second parallel guide slots, the sharps carrier having a block extending to engage the second parallel guide slots.

17. The retractable sharps assembly of claim 13 further comprising
    a cap removably positioned over the sharps member and extending through the first opening to outwardly of the housing, the cap being frangibly coupled with the frame, the sharps unit further including frangible rods extending between the sharps carrier and the frame.

* * * * *